United States Patent [19]

Alston, Jr.

[11] Patent Number: 4,502,489
[45] Date of Patent: Mar. 5, 1985

[54] APPARATUS FOR MEASURING AUDITORY REACTION TIME

[75] Inventor: William W. Alston, Jr., Palo Alto, Calif.

[73] Assignee: Audostart Corporation, Palo Alto, Calif.

[21] Appl. No.: 428,325

[22] Filed: Sep. 29, 1982

[51] Int. Cl.³ .............................................. A61B 5/16
[52] U.S. Cl. ..................................................... 128/746
[58] Field of Search ................ 128/746, 745; 434/258, 434/64, 264; 273/1 E, 16

[56] References Cited

U.S. PATENT DOCUMENTS

| | | | |
|---|---|---|---|
| 2,630,171 | 3/1953 | Allgaier | 434/64 |
| 3,698,385 | 10/1972 | Low et al. | 128/745 |
| 3,717,347 | 2/1973 | Hottendorf | 434/258 |
| 4,166,452 | 9/1979 | Generales | 128/746 |
| 4,169,592 | 10/1979 | Hall | 434/258 |

FOREIGN PATENT DOCUMENTS 163709 9/1963 U.S.S.R. ............................... 128/746
197857 4/1966 U.S.S.R. ............................... 128/746

Primary Examiner—William E. Kamm
Assistant Examiner—Francis J. Jaworski

[57] ABSTRACT

Apparatus is disclosed for measuring an athlete's auditory reaction time, and for training an athlete to reduce his auditory reaction time in response to an auditory stimulus used to initiate an athletic event. The apparatus automatically provides a sequence of variable time delays followed by auditory stimuli which stimulates the sequence and auditory quality of the preparatory commands used to initiate an athletic event. The apparatus further provides means for measuring and indicating the athlete's auditory reaction time in response to the auditory stimulus which represents the "Go" signal of the athletic event.

10 Claims, 7 Drawing Figures

APPARATUS FOR MEASURING AUDITORY REACTION TIME

BACKGROUND OF THE INVENTION

The invention described herein relates to apparatus for the measurement of auditory reaction time of human subjects and of human athletes in particular. The invention further relates to apparatus for training human athletes to reduce their auditory reaction time in response to the auditory stimuli used to initiate athletic events.

Many athletic events are initiated by auditory stimuli. Examples of such events include most running and swimming races in which gunshots or audible tones serve as the stimuli to which the participating athletes must respond and begin execution of the event. The delay between the onset of this stimuli and the beginning of the athlete's response is commonly referred to as auditory reaction time. Since the index of performance in such races is the time to complete the event, and since this time necessarily includes the athlete's delay in reacting to the auditory stimulus, it is of obvious importance to minimize the athlete's auditory reaction time.

Auditory reaction times in competitive races can be significant. Because individual differences in auditory reaction time often exceed the differences in finishing times of top competitors, it can be said that such races are won or lost in the first few tenths of a second.

The concept of training to improve auditory reaction time is not universally accepted, however. A common misconception among coaches and sports physiologists is that auditory reaction time is hereditary or somehow otherwise ingrained in an athlete and that it cannot be significantly improved. Part of the reason for this misconception is the limitation imposed by most common training methods. Often these training methods attempt to combine drills for auditory reaction time with the initial movements of the event itself. These initial movements typically involve substantial exertion and complex coordination among specific muscle groups, as in the first few steps of a running sprint race. Improvement of auditory reaction time using said combined drills is impaired both by the diversion of concentration to said complexity and by the number of possible repetitions being limited by said exertion.

Once it is recognized that auditory reaction time can be influenced through proper training, three major obstacles prevent logical development of this aspect of an athlete's performance.

First, means must be found to isolate auditory reaction time training from the complexity and exertion referred to above; the training process should require a minimum, if any, of the specific movements from the event itself. Any device used to assist auditory reaction time training must then be capable of being removed from the contest arena so that the athlete can be isolated from background noise, anxiety, and other potential impediments to performance.

Second, means must be developed to administer an auditory stimulus and then measure and record auditory reaction time in non-specific and isolated conditions and with an accuracy consistent with the hypothesis that differences measured in tenths of milliseconds may be significant.

Third, once non-specific auditory reaction time has been improved through isolated training, means must be provided to progressively reintroduce elements of the athletic event until the improved auditory reaction time becomes an integral part of the athlete's performance in said event. Such a progression might include gradual introduction of background noise by simply changing the environment or introduction of anxiety through contests of auditory reaction time with teammates, each stage of the progression serving to develop concentration and consistency of response.

The ideal training device for auditory reaction time should then provide means for isolating the athlete from all distractions, not only from the noise and anxiety of the arena but also from the mere presence of others. The device must therefore have means for permitting the athlete to initiate the typical preparatory commands and the timing process himself while still providing means to randomize and vary the onset of the auditory stimulus. The auditory stimulus must, for proper continuity, automatically simulate the quality and sequence of the auditory stimuli characteristic of the start of the athletic event of interest. Since the movement required of the athlete must be the minimum possible, means must be provided which is capable of detecting this minimum movement. The device must have means of accurately recording reaction time. Finally, in order to permit changes in environment, the device must be truly portable. This portability implies that the movement sensing means be capable of performing its function in all progressive stages of auditory reaction time training, from quiet, isolated room to the actual performance of the event in the athletic arena.

The prior art shows many devices which attempt to measure what is perceived by each inventor as the "reaction time" of a subject. However, none of these devices are adequate for measuring the auditory reaction time of the subject, nor for training athletes to reduce their auditory reaction time in response to the auditory stimuli used to initiate athletic events.

In nearly all of these prior art devices, the stimulus provided is visual. However, for the purposes of this invention a visual stimulus is inappropriate, since the device must simulate as closely as possible the stimuli used to initiate an athletic event. Visual stimuli are not employed for most athletic events for several reasons, e.g. starting positions are awkward for viewing such stimuli, and providing equivalent viewing angles for all the athletes participating in the event is nearly impossible. Thus, the stimuli for initiating these athletic events is auditory. It can readily be seen, therefore, that any device for training an athlete to reduce his reaction time to the stimulus used to initiate an athletic event must be capable of producing an auditory stimulus. This is further emphasized by the fact that the signal pathways in the nervous system, and specifically the areas of the brain, that process auditory and visual stimuli are quite different, resulting in an athlete's response to visual stimuli being different from his response to auditory stimuli. This difference in response means that training to reduce visual reaction times (and the resulting reaction times) is not the equivalent of training to reduce auditory reaction times.

The prior art devices differ from the apparatus of the invention in several other significant ways. For example, these devices do not generally provide for the automatic sequencing of the stimuli; in fact, the stimulus is typically provided by a second party. More importantly, the means employed for detecting the subject's response to the stimulus incurs significant error in that it requires the subject to perform some task, in some cases a very complex one, which combines and renders inseparable the time required to execute this task with the time needed to first react to the stimulus with a minimum movement. When placed in the context of this invention, these prior art devices are incapable of measuring auditory reaction time (or even visual reaction time) because their timing means are not deactivated at the end of the time period which represents auditory (or visual) reaction time, but rather at the end of the time period which represents auditory (or visual) reaction time plus the time required to complete some physical task.

Such prior art devices are disclosed in, for example, U.S. Pat. No. 2,630,171 to Allgaier which relates to a device which purports to measure the average time required by a person to respond to an external stimulus, e.g. to react to a traffic stop signal by taking some action simulating the application of foot pressure to the brake pedal of an automobile. However, the disclosed device does not provide for an auditory stimulus, nor does it provide any means for the automatic sequencing of stimuli. Furthermore, Allgaier's device requires a specific, complex movement on the part of the user before the means timing the so-called "reaction time" is deactivated. Thus, Allgaier's device does not measure, and, in fact, is incapable of measuring only the subject's auditory reaction time.

U.S. Pat. No. 3,717,347 to Hottendorf discloses a device for testing what Hottendorf perceives as a subject's "reaction time". The device consists basically of a vertical slot or channel into which a coin is inserted. At some random time after the subject depresses a "gas pedal" the coin is dropped into the channel. A braking linkage is then depressed by the subject to catch the coin fall as rapidly as possible.

As with Allgaier's device, Hottendorf's mechanism provides only a visual stimulus to the user, and requires a specific, complex movement in response to it. Also, the manner of "timing" the subject's response, i.e. indicating how far the coin has fallen when the brake is activated, is very crude and imprecise. While Hottendorf does provide for a random delay between the time the coin is inserted into the channel and the time of its release, no means is provided for automatically sequencing a series of stimuli.

U.S. Pat. No. 4,169,592 to Hall discloses an electronic reflex game wherein one of a plurality of switches is manipulated by a player to deactivate one of a plurality of lights which are randomly actuated. As with the previously discussed patents, the stimulus employed is visual, the required response is complex, and the device tests something other than auditory reaction time. More importantly, however, the user is required to make a conscious decision as to which particular response is required depending upon the particular stimulus provided, i.e., he must not only react to the lighting of a lamp, he must also deactivate the correct lamp. Thus, the user must perceive the stimulus, decide on the particular physical response to be made, and make and complete the response before the "test" or "game" is considered complete. As is readily apparent, the addition of the decision phase of the required response adds another variable, inseparable factor to the total response time.

U.S. Pat. No. 3,698,385 to Low et al discloses a reaction tester for testing the simple and disjunctive reaction of a subject to light stimulus. While the movement required on the part of the user in response to the stimulus is not as complex as that required by the previously discussed devices, the user is required to make a decision as to which of three possible responses he should make. This decision phase is undesireable in the Low et al device for the same reason discussed with regard to the Hall device.

SUMMARY OF THE INVENTION

The present invention provides apparatus for measuring an athlete's auditory reaction time, and for training the athlete to reduce his auditory reaction time in response to an auditory stimulus used to initiate an athletic event. The apparatus of this invention overcomes many of the disadvantages and shortcomings of prior art "reaction time" measuring devices. In accordance with this invention, there is provided apparatus for measuring an athlete's auditory reaction time, and for training an athlete to reduce his auditory reaction time in response to an auditory stimulus used to initiate an athletic event comprising:

(a) means for actuating the apparatus;

(b) auditory stimulus-producing means capable of simulating an auditory stimulus used to initiate an athletic event;

(c) sensing means capable of detecting a minimum movement made by the athlete;

(d) first variable delay means connected to the means for actuating the apparatus, and responsive to said means for actuating the apparatus, for providing a first variable time period following the actuation of the apparatus; said first variable delay means being further connected to the auditory stimulus-producing means and being capable of causing a first actuation of the auditory stimulus-producing means at the end of said first variable time period;

(e) second variable delay means connected to the auditory stimulus-producing means, and responsive to the auditory stimulus-producing means, for providing a second variable time period following the first actuation of the auditory stimulus-producing means; said second variable delay means being capable of causing a second actuation of the auditory stimulus-producing means at the end of said second variable time period;

(f) timing means connected to the auditory stimulus-producing means, and responsive to said auditory stimulus-producing means and being activated by the onset of the second actuation of the auditory stimulus-producing means;

(g) means for deactivating the timing means connected to the timing means and being further connected to the sensing means and responsive to said sensing means; said means for deactivating the timing means being capable of deactivating said timing means when the athlete makes a minimum movement which is detectable by said sensing means; and, (h) display means connected to the timing means, said display means being capable of displaying the time measured by said timing means.

The apparatus thus provides an automatic sequence of variable time delays followed by auditory stimuli which simulates the preparatory commands used to initiate an athletic event, and measures and displays the athlete's auditory reaction time in response thereto.

DESCRIPTION OF THE PREFERRED EMBODIMENTS

Figure 1:
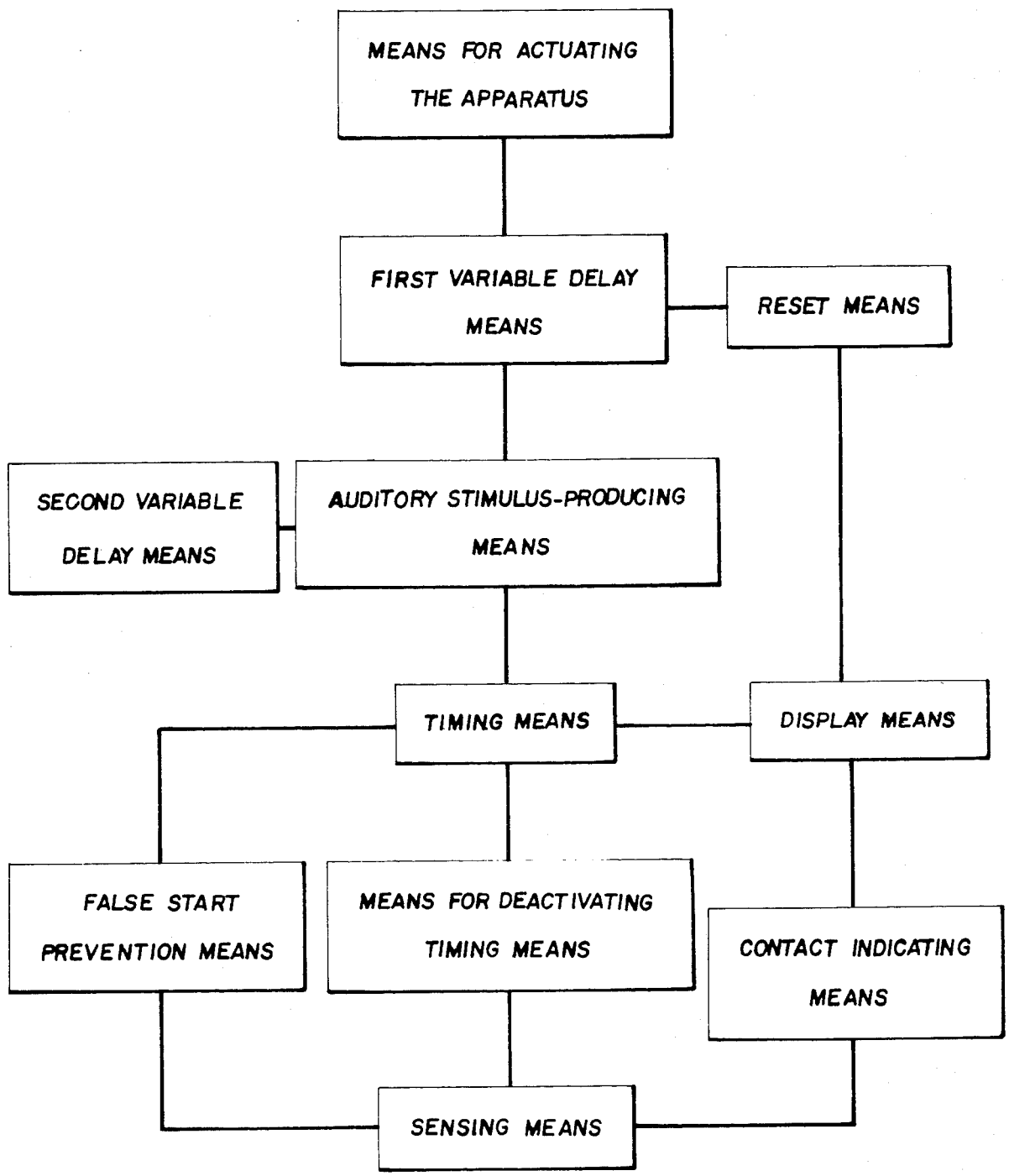
FIG. 1 is a schematic representation of the apparatus of this invention.

Referring to FIG. 1, the apparatus of this invention includes means for actuating the apparatus which is connected to a first variable delay means. Since it is contemplated that the apparatus is electrically powered, the means for actuating the apparatus may conveniently be a simple electrical switch which actuates the apparatus by closing an electrical circuit. The first variable delay means is responsive to the actuation of the apparatus and is activated thereby. Once activated, the first variable delay means provides a first variable time period commencing with the activation of the first variable delay means, the duration of said first variable time period being determined by the first variable delay means. At the end of this first variable time period, the first variable delay means activates, for a first time, the auditory stimulus-producing means, to which the first variable delay means is connected.

A second variable delay means is connected to the auditory stimulus-producing means. This second variable delay means is responsive to and activated by the first activation of the auditory stimulus-producing means. The second variable delay means provides a second variable time period commencing with the first actuation of the auditory stimulus-producing means, the duration of this second variable time period being determined by the second variable delay means. At the end of this second variable time period, the second variable delay means actuates the auditory stimulus-producing means a second time.

The auditory stimulus-producing means is connected to a timing means. The timing means is responsive to the second actuation of the auditory stimulus-producing means and is activated immediately upon the onset of the second actuation of the auditory stimulus-producing means.

The apparatus is also provided with a sensing means which is capable of detecting a minimum movement made by the athlete. The sensing means is connected to means for deactivating the timing means, said means for deactivating the timing means being in turn connected to the timing means. When the athlete makes a minimum movement which is detectable by the sensing means, said sensing means actuates the means for deactivating the timing means, thereby causing the timing means to stop its timing function. Display means is connected to the timing means which is capable of displaying the time measured by the timing means, i.e. the time period commencing with the timing means' activation by the second actuation of the auditory stimulus-producing means and ending with the timing means' deactivation by the means for deactivating the timing means.

In a preferred embodiment of the invention, the apparatus also includes a false start prevention means. The purpose of the false start prevention means is to ensure that the timing means will not be deactivated in response to a minimum movement made by the athlete which is detectable by the sensing means and which minimum movement occurs prior to the onset of the second actuation of the auditory stimulus-producing means. The false start prevention means is connected to the sensing means and is responsive to the sensing means. The false start prevention means is further connected to the timing means and is capable of disabling the timing means, i.e. preventing it from beginning its timing function, in the event the sensing means detects a minimum movement made by the athlete prior to the second actuation of the auditory stimulus-producing means.

In another preferred embodiment, the apparatus is provided with a reset means which allows the athlete to clear the display means of the time displayed after a first use of the apparatus and reactivate the apparatus, thereby preparing the apparatus for another use. The reset means is connected to the display means and is capable of clearing the time displayed by said display means. The reset means is further connected to the first variable delay means and is capable of activating said first variable delay means which will start the apparatus on another automatic performance of its function.

The various means employed by the apparatus of this invention will now be described in greater detail.

The first variable delay means may be any mechanical or, preferably, electronic means which is capable of providing a first variable time period following actuation of the apparatus, and which is capable of actuating the auditory stimulus-producing means at the end of the first variable time period. The first time period may be variable either manually or automatically by the first variable delay means itself. Preferably, the manner in which the time period is varied, whether manually or otherwise, will be such that the duration of the resulting time period will not be predictable by the athlete.

The second variable delay means may be any mechanical or, preferably, electronic means which is capable of providing a second variable time period following the first actuation of the auditory stimulus-producing means and which is capable of actuating the auditory stimulus-producing means a second time at the end of the second variable time period. As with the first variable delay means, the second time period may be variable either manually or automatically by the second variable delay means itself, and the resulting time period should not be predictable by the athlete.

It should be noted that the first and second variable time periods may be of equal or different duration, the duration of each being from about 1 to about 15 seconds.

It should be emphasized that, while the variable delay means are described herein in terms of a first and second variable delay means, it is contemplated that the first and second variable time periods may be provided by a single variable delay means which is capable of providing both the first and second variable time periods, and that such single variable delay means should be considered the equivalent of separate first and second variable delay means.

Figure 3:
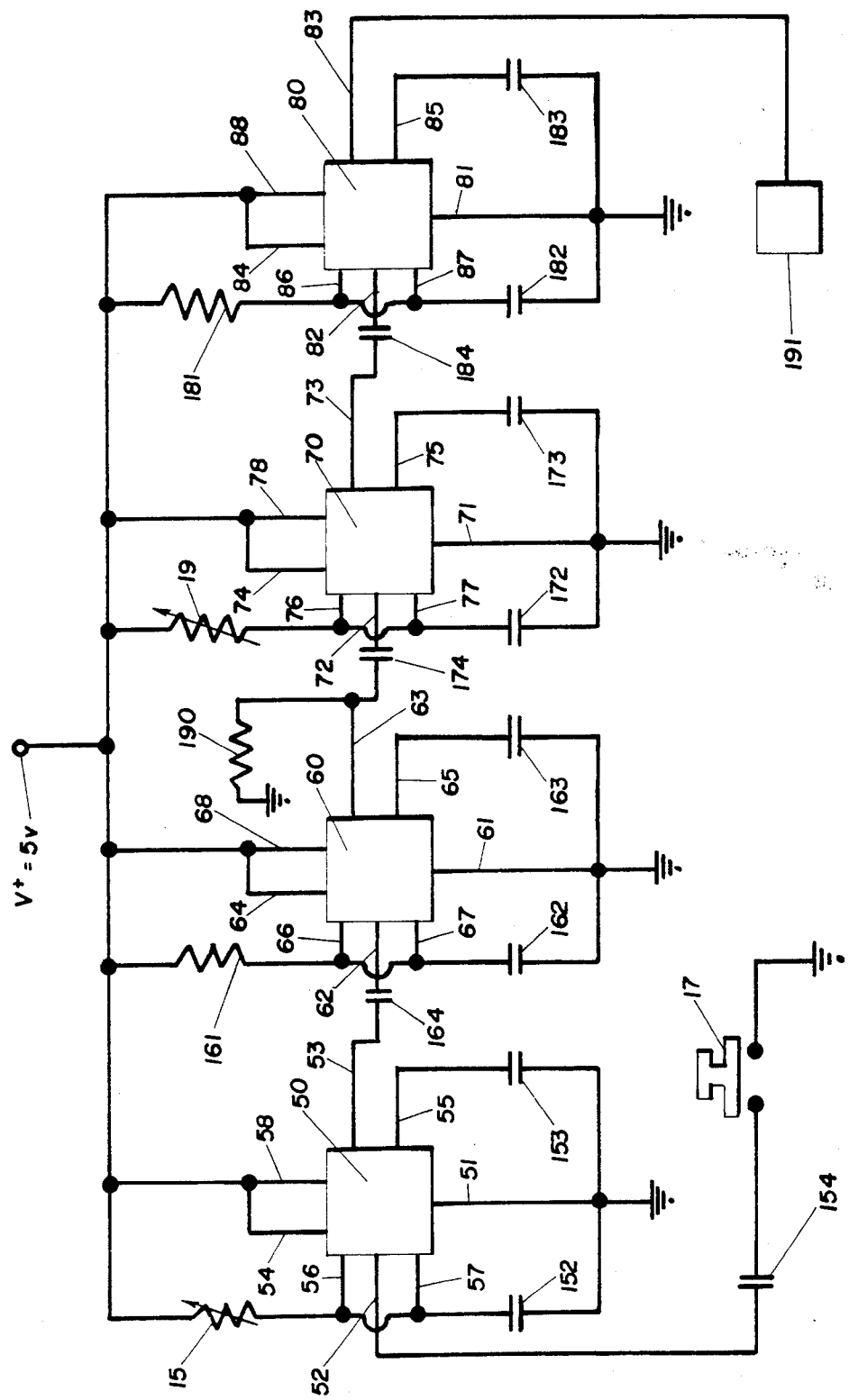
FIG. 3 is a schematic wiring diagram showing one embodiment of the means for actuating the apparatus, and the first and second variable delay means employed in the apparatus of this invention.

A preferred embodiment of the first and second variable delay means is shown schematically in FIG. 3. The first and second variable delay means comprise four NE 555 integrated circuit timers 50, 60, 70 and 80 with associated passive components. (Timers other than the NE 555 timers may, of course, be employed such as, for example, timing chips such as a 556 dual 555 chip, a 322 or 3905 precision timer, and 2240, 2250 or 8260 programmable timer counter, to name a few). Said timers are assembled in concert, as described below.

Initially, the circuitry of the first and second variable delay means is powered at 5 v as shown in FIG. 3 and is held in standby state. Output pins 53, 63, 73 and 83 of the four timers are held at a low voltage state, near ground level. When the apparatus is actuated by closing normally open pushbutton switch 17, a negative-going pulse is delivered through capacitor 154 to the trigger pin 52 of timer 50, thereby forcing output pin 53 to a high voltage state near V+ and beginning the time period, i.e. the first variable time period, of said timer. The duration of the timing period is controlled by the combination of the fixed value of capacitor 152 and the variable resistance provided by potentiometer 15. At the end of the timing period, pin 53 falls once again to a low voltage state, thereby delivering a negative-going pulse through capacitor 164 to trigger pin 62 of timer 60. Output pin 63 is forced to a high voltage state, actuating the auditory stimulus-producing means 190 for a period controlled by the fixed values of capacitor 162 and resistor 161.

At the end of the timing period of timer 60, the output pin 63 falls once again to a low voltage state, thereby interrupting power to the auditory stimulus-producing means 190 and simultaneously delivering a negative-going pulse through capacitor 174 to trigger pin 72 of timer 70, thereby forcing output pin 73 to a high voltage state and beginning the timing period, i.e. the second variable time period, for timer 70, said timing period being controlled by the fixed value of the capacitor 172 and the variable resistance provided by potentiometer 19. At the end of the timing period of timer 70, output pin 73 falls once again to a low voltage state, thereby delivering a negative-going pulse through capacitor 184 to trigger pin 82 of timer 80, shifting voltage at output pin 83 to a high state. This high voltage state at pin 83 is used to actuate auditory stimulus-producing means 191.

The duration of the stimulus produced by auditory stimulus-producing means 191 is determined by timer 80 which is controlled by the fixed values of capacitor 182 and resistor 181, said stimulus duration typically being on the order of 0.5 seconds. Capacitors 153, 163, 173, and 183 are included to provide noise immunity. Table I provides typical values of capacitors and resistors within the first and second variable delay means circuitry illustrated in FIG. 3. Table II identifies the pins of each of the NE 555 timers in FIG. 3.

TABLE I

| TIMER NO. | TIMING CAPACITOR NO. | μF | TIMING RESISTOR NO. | KΩ | TRIGGER CAPACITOR NO. | μF | NOISE SUPPRESSION CAPACITOR No. | μF |
|---|---|---|---|---|---|---|---|---|
| 50 | 152 | 10.0 | 15 | 0.5–10 | 154 | 0.001 | 153 | 0.01 |
| 60 | 162 | 1.0 | 161 | 50 | 164 | 0.001 | 163 | 0.01 |
| 70 | 172 | 1.0 | 19 | 1000–6000 | 174 | 0.001 | 173 | 0.01 |
| 80 | 182 | 3.0 | 181 | 500 | 184 | 0.001 | 183 | 0.01 |

TABLE II

| DESCRIPTION | FIGURE NUMBERS | | | |
|---|---|---|---|---|
| Timer | 50 | 60 | 70 | 80 |
| Ground Pin | 51 | 61 | 71 | 81 |
| Trigger Pin | 52 | 62 | 72 | 82 |
| Output Pin | 53 | 63 | 73 | 83 |
| Reset Pin | 54 | 64 | 74 | 84 |
| Control Voltage Pin | 55 | 65 | 75 | 85 |
| Threshold Pin | 56 | 66 | 76 | 86 |
| Discharge Pin | 57 | 67 | 77 | 87 |
| Vcc Pin | 58 | 68 | 78 | 88 |

The auditory stimulus-producing means employed in the apparatus may be any means capable of simulating an auditory stimulus used to initiate an athletic event. Typically, in an athletic event such as a running sprint race, the stimuli used to initiate the event are the verbal command "On your marks." (followed by a first variable delay), the verbal command "Get set." or simply "Set." (followed by a second variable delay) and a gunshot which indicates the actual start of the race. Of course, other auditory stimuli may be used to initiate other athletic events, such as swimming races, football plays and the like, and it is, therefore, intended that any means which is capable of simulating such other stimuli are included in the definition of the term "auditory stimulus-producing means" as used herein.

It should be emphasized that the stimuli produced by the first and second actuations of the auditory stimulus-producing means may be alike or different. In those cases where it is desireable that the auditory stimuli be different, as where the first is a verbal command "Get set." and the second is a gunshot, the different stimuli may be produced by a single auditory stimulus-producing means. However, two separate auditory stimulus-producing means may also be used, each producing one of the stimuli, without deviating from the spirit and scope of the invention.

While it is not critical what particular auditory stimulus-producing means is employed, e.g. a buzzer, bell, simulated gunshot, simulated verbal command, or tape recording, it is essential that the auditory stimulus produced simulate as nearly as possible the actual stimulus used to initiate the particular event for which the athlete is training. By this close simulation of the actual stimulus, the athlete's training on the apparatus can most accurately correlate to his response to the stimulus in actual performance of the event.

Figure 4:
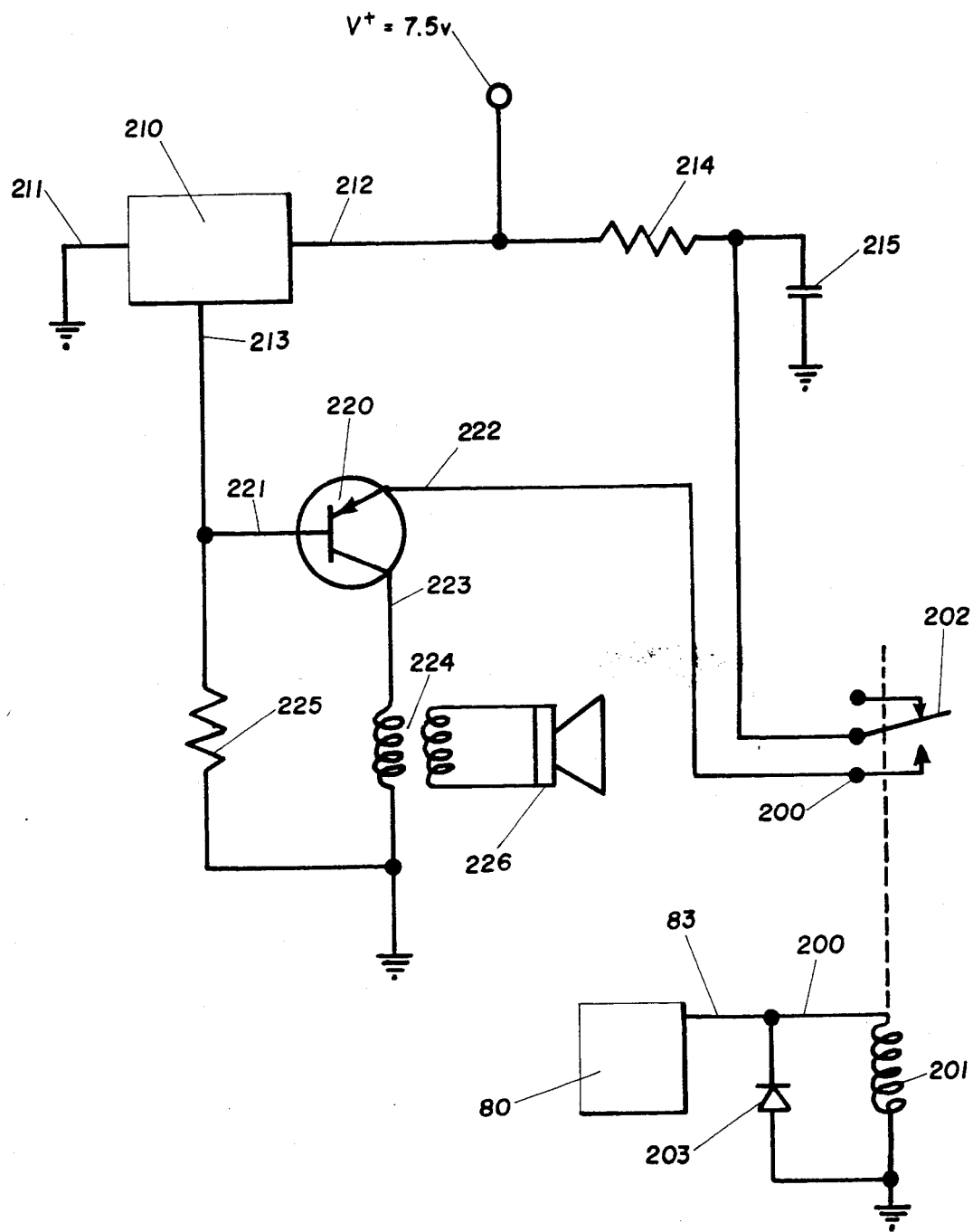
FIG. 4 is a schematic wiring diagram showing one embodiment of the auditory stimulus-producing means employed in the apparatus of this invention.

In one embodiment of the invention, the auditory stimulus consists of an electronically simulated gunshot sound, such as that generated by the circuitry shown schematically in FIG. 4. Pseudorandom white noise generator 210, typically Radio Shack catalogue number 276-1768, is powered continuously at 7.5 volts at V+ pin 212, while ground pin 211 is connected to ground. Output pin 213 is connected to the base 221 of transistor 220, typically PNP type M2N5401 or equivalent. A white noise signal is thereby constantly delivered to base 221. Resistor 225 serves as a base biasing resistor for transistor 220. The 7.5 volt input keeps capacitor 215, typically 100uF electrolytic type, in a fully charged state.

As output pin 83 of timer 80 from FIG. 3 goes to a high voltage state, this higher voltage supplies power simultaneously to relay 200, typically a miniature reed type with internal diode 203. Relay 200, on receiving power to coil 201, closes contacts 202, and discharges capacitor 215 through collector 222 of transistor 220, thereby amplifying the white noise signal at base 221 and delivering said amplified signal at emitter 223 through transformer 224, thus driving speaker 226. Because the power to collector 222 comes from the discharge of capacitor 215, the sound produced decays quickly, in a manner similar to the sound of an actual gunshot. Varying the value of capacitor 215 can change this decay rate. Resistor 214, typically on the order of 10KΩ, is sized to allow charging capacitor 215 while limiting the flow of current so that once capacitor 215 is discharged, the amplified white noise signal is reduced to an inaudible level at speaker 226. In another embodiment, transistor 220 is replaced by a higher output integrated circuit amplifier with sound level adjustment.

When output pin 83 of timer 80 falls to a low voltage state, relay contacts 202 open and capacitor 215 returns to a fully charged condition. Another gunshot sound can then be generated by repeating the sequence described above.

The sensing means useful in the apparatus of this invention may be any mechanical or, preferably, electronic means which is capable of detecting a minimum movement made by the athlete and of actuating the means for deactivating the timing means when such a minimum movement is detected by the sensing means. The term "minimum movement", as used herein, refers to the initiation of any simple, non-specific movement made by the athlete in response to the auditory stimulus. It should be emphasized that the apparatus of this invention measures the time from the onset of the second actuating of the auditory stimulus-producing means until the athlete initiates a physical response thereto. Thus, it is critical that the sensing means be capable of detecting as accurately and quickly as possible the initiation of the athlete's minimum movement. It is not sufficient that the sensing means detect only the completion of the athlete's movement, as would be the case where the athlete would be required to, e.g., flip a switch, step on a pedal or grasp an object, before his response could be detected by the sensing means.

A simple, normally-open spring loaded pushbutton switch may be employed as the sensing means. In this case, the athlete would hold the switch in the closed position prior to the onset of the second auditory stimulus. Once the second auditory stimulus occurs, the timing means would begin to function. The athlete would respond to the second auditory stimulus by simply releasing the pushbutton and thereby opening the switch. The opening of the switch would actuate the means for deactivating the timing means and the timing means would stop.

In a preferred embodiment, the sensing means is an electronic touchplate. The electronic circuitry associated with the touchplate provides means for detecting the changes in electrical resistance and capacitance of the plate when the skin of the athlete, e.g. his finger or hand, contacts the touchplate. If an SE/NE 555 integrated circuit timer, or equivalent circuit, is used as the basis for said circuitry, the circuit's response to the removal of skin from the touchplate typically occurs within seventeen microseconds. This circuit response would typically consist of an output voltage shift coincident with skin contact on the touchplate. This output voltage shift can be used in a further preferred embodiment whereby the sensing means is connected to means for indicating the athlete's proper contact with the sensing means. The contact indicating means may conveniently be further connected to the display means which would indicate proper contact in any convenient manner, such as by clearing the display means of its display for as long as proper contact is maintained with the sensing means and until the display means begins to display the time measured by the timing means.

The advantages of employing an electronic touchplate as the sensing means are readily apparent. As noted above, proper contact with the touchplate can be confirmed. Only the absolute minimum movement on the part of the athlete is required for detection by the sensing means, and the electronic response of the touchplate is extremely high speed. Also, simple adaptation to the athletic arena is possible.

Figure 5:
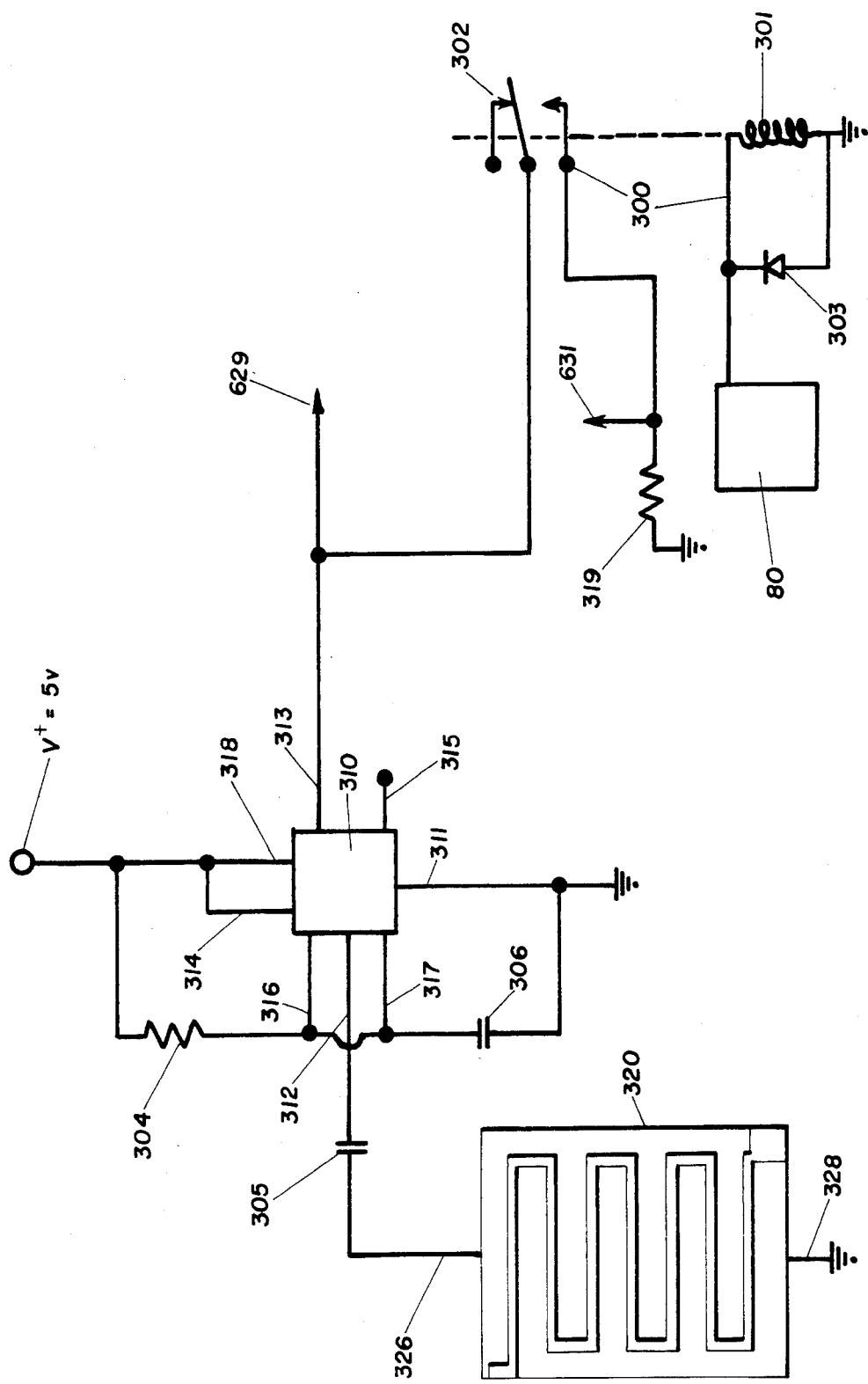
FIG. 5 is a schematic wiring diagram showing one embodiment of the sensing means, the means for deactivating the timing means and the contact indicating means employed in the apparatus of the invention.
Figure 6:
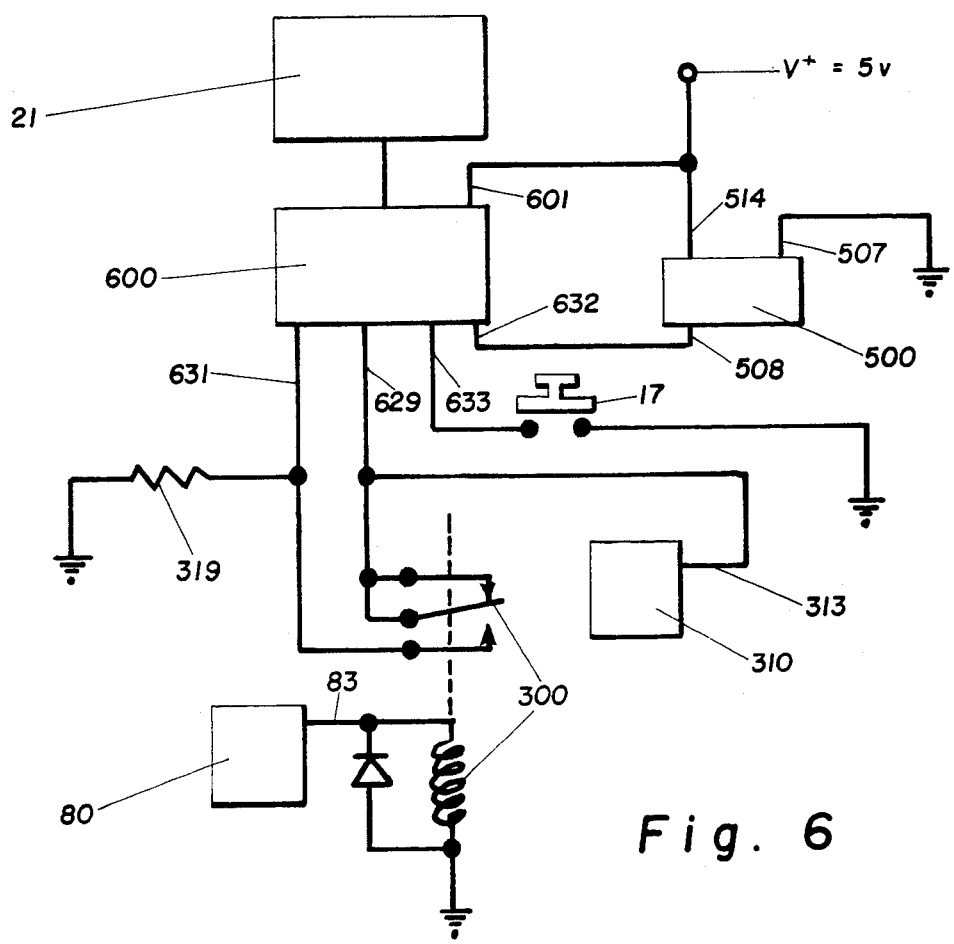
FIG. 6 is a schematic wiring diagram showing one embodiment of the sensing means, contact indicating means, display means, timing means, and reset means employed in the apparatus of this invention.
Figure 7:
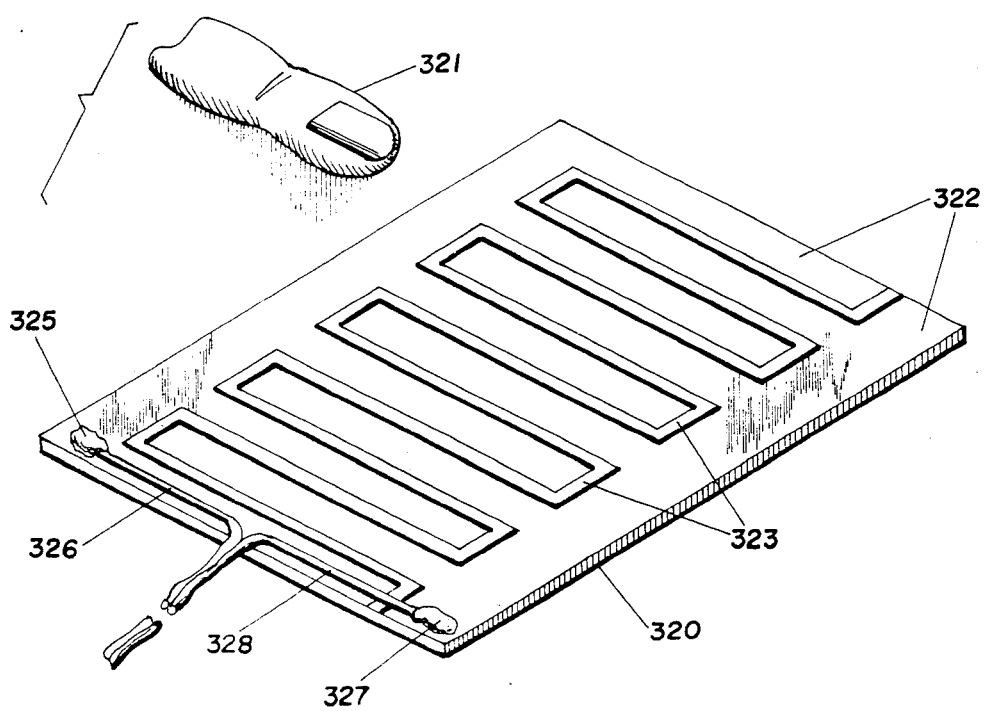
FIG. 7 is a perspective view illustrating one embodiment of the sensing means employed in this invention.

A preferred embodiment of the sensing means and contact indicating means are illustrated in FIGS. 5, 6 and 7. An NE 555 timer 310 is powered at +5v continuously with associated passive components shown in FIG. 5.

Touch plate 320 is a copper clad fiberglass board, of a type typically used for print circuits, with portions of the copper 322 etched away to expose the fiberglass 323 in a design similar to that shown in FIG. 7. Approximately one-half of the copper design is connected by solder joint 325 to insulated wire 326, which in turn is connected through capacitor 305 in FIG. 5 to trigger pin 312 of timer 310, while the other half of the copper design is connected by solder joint 327 through insulated wire 328 to ground. As the skin of the athlete's finger 321 comes in contact with the touchplate 320, said skin lowers the electrical resistance between the two copper sections of the design, thereby providing a minute current path between capacitor 305 and ground. In this manner, the athlete's finger 321 coming into contact with touchplate 320 causes a negative-going pulse to be delivered to trigger pin 312 of timer 310, driving output pin 313 from low to high voltage state. Output pin 313 will remain in a high voltage state until the athlete's finger 321 is removed from touchplate 320, at which time output pin 313 will return to a low voltage state.

Output pin 313 of timer 310 is connected to the display means via the leading zero blanking function pin 629 of counter 600. Skin contact with the touchplate 320 causes output pin 313 to go to a high voltage state and zeros on the 4½ liquid crystal display 21 are blanked. Removing skin contact from touchplate 320 causes zeros on the 4½ liquid crystal display 21 to reappear. Contact indicating means is thus provided and evidence of proper skin contact with touchplate 320 is thereby provided to the athlete.

Table III provides typical values of capacitors and resistors within the sensing means and contact indicating means represented by FIG. 5 and 6. Table IV below identifies the pins of timer 310.

TABLE III

| Timing No. | Capacitor μF | Timing No. | Resistor KΩ | Trigger No. | Capacitor μF |
|---|---|---|---|---|---|
| 306 | .01 | 304 | 1.0 | 305 | 1.0 pF |

TABLE IV

| Description | FIG. NO. |
|---|---|
| Timer | 310 |
| Ground Pin | 311 |
| Trigger Pin | 312 |
| Output Pin | 313 |
| Reset Pin | 314 |
| Control Voltage Pin (not connected) | 315 |
| Threshold Pin | 316 |
| Discharge Pin | 317 |
| Vcc Pin | 318 |

The timing means may be any mechanical or, preferably, electronic means capable of measuring time. Since the auditory reaction times to be measured by the apparatus are extremely short, and, since the apparatus must be able to measure and indicate the even shorter times which represent the difference between two auditory reaction times (either of two athletes or between two uses of the apparatus by the same athlete), it is essential that the timing means be capable of measuring time in extremely small units, e.g. in milliseconds (0.001 second) and preferably in tenths of milliseconds (0.0001 second). The timing means must also be capable of providing accurate and consistent time measurement for each use of the apparatus.

A preferred embodiment of the timing means is illustrated in FIG. 6. An oscillator 500, typically a 10 Khz oscillator, such as a Connor-Winfield CMOS Model C15R5 a dual inline package, is powered at 5v continuously at V+ pin 514 and grounded at ground pin 507, producing a 10 Khz±0.01% squarewave at output pin 508. Said 10 Khz output is connected to counter input pin 632 of a counter 600, such as a Datel-Intersil Model ICM 7224 counter/decoder/driver in a standard 40-pin dual inline package. The counter, powered through V+ power supply pin 601 at 5 v, counts said squarewave, converts the counts to decimal, and drives a liquid crystal display 21, such as an A.N.D. 4½ digit display model FE0206, through appropriate pin-connections, not shown. Time is thus displayed as seconds, tenths, hundredths, thousandths, and tenths of thousandths of seconds on the 4½ digit liquid crystal display 21.

Connected as described, the timing means and display means would count and display time continuously except for three control functions on counter 600. First, if count inhibit pin 631 is held at a low voltage state, counting of 10 Khz squarewave output at pin 632 is discontinued. This low voltage state is maintained at pin 631 by connection through resistor 319, typically 10 K ohms–100 K ohms, to ground. Counting is initiated by raising pin 631 to a high voltage state when relay 300 to the auditory stimulus-producing means (typically a miniature reed type with internal diode 303) has been closed simultaneously with the onset of the auditory stimulus thereby sending power from coil 301 to close contact 302. However, counting is initiated only if the sensing means provides a high voltage at output pin 313 in response to the athlete's finger 321 making contact with touchplate 320. See FIG. 6.

Second, the counter 600 and liquid crystal display 221 can be reset by the reset means. The reset means may be any mechanical or, preferably, electronic means which allows the athlete to clear the display means of the time displayed after a first use of the apparatus, and reactivate the apparatus, thereby preparing the apparatus for another use.

A preferred embodiment of the reset means is illustrated in FIG. 6. The counter 600 and liquid crystal display 21 can be reset to zero by connecting reset pin 633 to ground. This reset operation is accomplished by closing normally open pushbutton 17 which clears the display and reactivates the first variable delay means. See FIG. 3.

The third control function on counter 600 keeps the leading zero blanking pin 629 at a high voltage state through the athlete's contact with touchplate 320, thereby blanking 4½ digit liquid crystal display 21 and serving as an indicator of the athlete's contact with touchplate 320.

The means for deactivating the timing means may be any mechanical or, preferably, electronic means which is capable of causing the timing means to stop its timing function when the athlete makes a minimum movement which is detectable by the sensing means.

A preferred embodiment of the means for deactivating the timing means is illustrated in FIG. 5. The timer 310 of the timing means provides output voltage via output pin 313 to counter 600 of FIG. 6. This output voltage from pin 313 is maintained at a high voltage state when the touchplate 320 is touched by the athlete and drops to a low voltage state when contact is broken. When the output voltage of pin 313 drops to this low state, counter 600 is deactivated and the timing means ceases to perform its timing function. Resistor 319 prevents any stray voltage from allowing the timing means to continue to function after the output voltage at pin 313 drops to its low state.

The apparatus is extremely simple to operate. The athlete need only actuate the apparatus via the means for actuating the apparatus. The apparatus then automatically performs its functions and provides, in sequence, a first variable time period, a first auditory stimulus, a second variable time period and a second auditory stimulus. Upon hearing the second auditory stimulus, the athlete makes a minimum movement which is detected by the sensing means, e.g. breaking skin contact with a touchplate, and his auditory reaction time is displayed automatically. To use the apparatus again he either reactuates the apparatus via the apparatus actuating means, or, if reset means are provided, activates the reset means.

Figure 2:
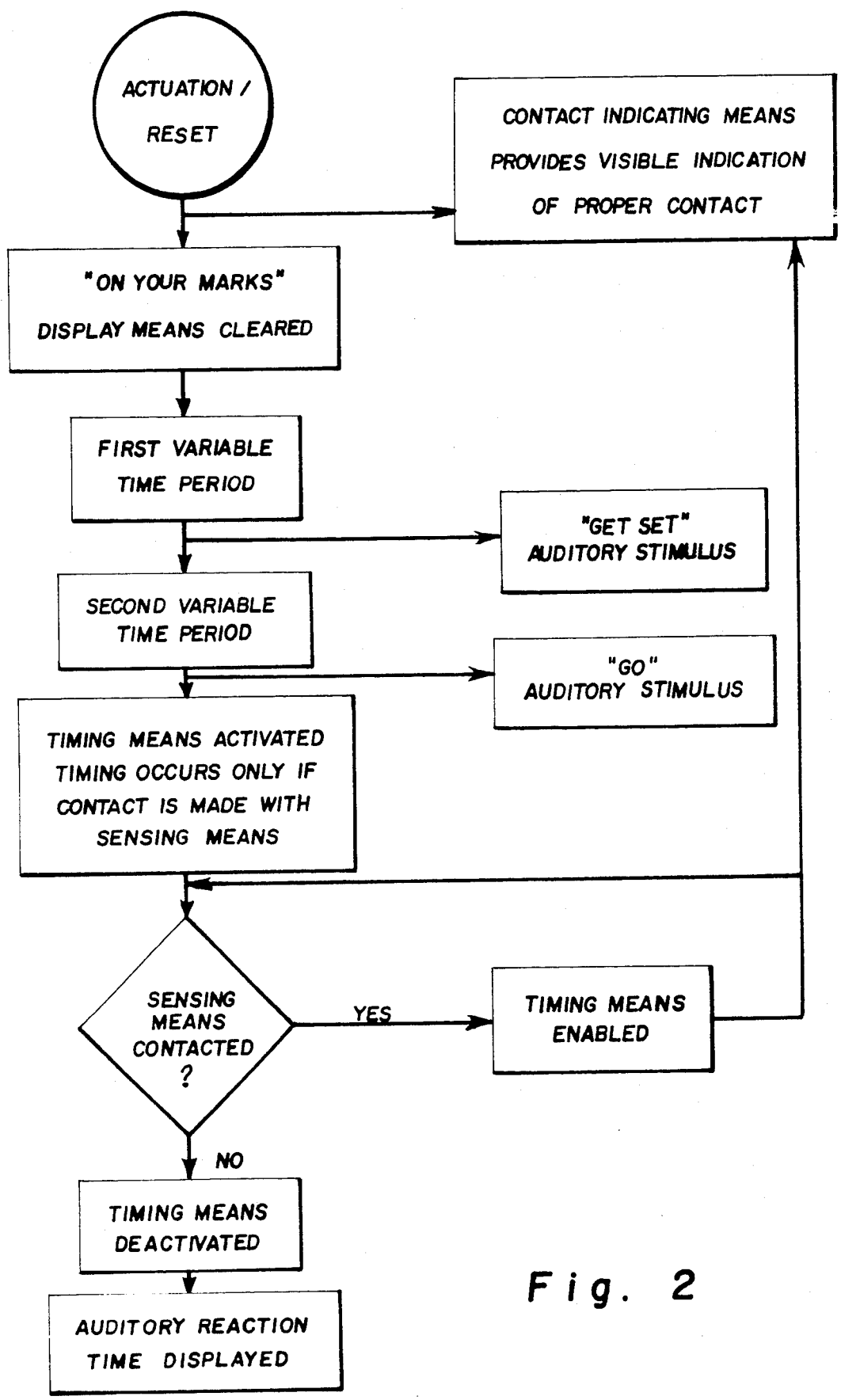
FIG. 2 is a flow chart showing the method in which the apparatus of this invention operates.

The flow chart in FIG. 2 provides further explanation of the method by which a preferred embodiment of the apparatus operates. When the apparatus is actuated, the display means is cleared of any previously displayed time. This represents the classic "On your marks." command of an athletic event. A first variable time period follows the actuation of the apparatus. At the end of this first variable time period, the apparatus automatically activates the auditory stimulus-producing means, a first time, thereby providing the equivalent of a "Get set." command. A second variable time period follows the first auditory stimulus and, at the end of the second variable time period, the apparatus automatically activates the auditory stimulus-producing means a second time, thereby providing the equivalent of a "Go." command. The timing means is activated simultaneously with the second activation of the auditory stimulus-producing means, but only if the proper contact is made with the sensing means. The display means provides a visible indication of such proper contact. If proper contact is made with the sensing means, the timing means begins its timing function until it is deactivated when the sensing means detects a minimum movement made by the athlete. The display means then displays the time measured by the timing means.

Other features, advantages and specific embodiments of this invention will become readily apparent to those exercising ordinary skill in the art after reading the foregoing disclosures. These specific embodiments are within the scope of the claimed subject matter unless otherwise expressly indicated to the contrary. Moreover, while a few specific embodiments of this invention have been described in considerable detail, variations and modification of these embodiments can be effected without departing from the spirit and scope of the invention as disclosed and claimed.

What I claim is:

1. Apparatus for measuring an athlete's auditory reaction time, and for training an athlete to reduce his auditory reaction time in response to an auditory stimulus used to initiate an athletic event comprising:
    (a) means for actuating the apparatus;
    (b) auditory stimulus-producing means capable of simulating an auditory stimulus used to initiate an athletic event;
    (c) sensing means capable of detecting a minimum movement made by the athlete;
    (d) first variable delay means connected to the means for actuating the apparatus, and responsive to said means for actuating the apparatus, for providing a first variable time period following the actuation of the apparatus; said first variable delay means being further connected to the auditory stimulus-producing means and being capable of causing a first actuation of the auditory stimulus-producing means at the end of said first variable time period;
    (e) second variable delay means connected to the auditory stimulus-producing means, and responsive to the auditory stimulus-producing means, for providing a second variable time period following the first actuation of the auditory stimulus-producing means; said second variable delay means being capable of causing a second actuation of the auditory stimulus-producing means at the end of said second variable time period;
    (f) timing means connected to the auditory stimulus-producing means, and responsive to said auditory stimulus-producing means and being activated by the onset of the second actuation of the auditory stimulus-producing means;
    (g) means for deactivating the timing means connected to the timing means and being further connected to the sensing means and responsive to said sensing means; said means for deactivating the timing means being capable of deactivating said timing means when the athlete makes a minimum movement which is detectable by said sensing means; and,
    (h) display means connected to the timing means, said display means being capable of displaying the time measured by said timing means.

2. The apparatus of claim 1 wherein the sensing means is an electronic touchplate.

3. The apparatus of claim 2 comprising false start prevention means connected to the sensing means and responsive to said sensing means, and further connected to the timing means, said false start prevention means being capable of disabling the timing means in the event the sensing means detects a minimum movement made by the athlete prior to the second actuation of the auditory stimulus-producing means.

4. The apparatus of claim 3 further comprising reset means connected to the display means and further connected to the first variable delay means, said reset means being capable of actuating the apparatus a second time after a first use of the apparatus by clearing the time displayed by the display means and actuating the first variable delay means.

5. The apparatus of claim 4 further comprising contact indicating means connected to the sensing means and responsive to the sensing means, and further connected to the display means, said contact indicating means being capable of indicating proper contact by the athlete with the sensing means.

6. The apparatus of claim 2 further comprising reset means connected to the display means and further connected to the first variable delay means, said reset means being capable of actuating the apparatus a second time after a first use of the apparatus by clearing the time displayed by the display means and actuating the first variable delay means.

7. The apparatus of claim 2 further comprising contact indicating means connected to the sensing means and responsive to the sensing means, and further connected to the display means, said contact indicating means being capable of indicating proper contact by the athlete with the sensing means.

8. The apparatus of claim 1 comprising false start prevention means connected to the sensing means and responsive to said sensing means, and further connected to the timing means, said false start prevention means being capable of disabling the timing means in the event the sensing means detects a minimum movement made by the athlete prior to the second actuation of the auditory stimulus-producing means.

9. The apparatus of claim 1 further comprising reset means connected to the display means and further connected to the first variable delay means, said reset means being capable of actuating the apparatus a second time after a first use of the apparatus by clearing the time displayed by the display means and actuaing the first variable delay means.

10. The apparatus of claim 1 further comprising contact indicating means connected to the sensing means and responsive to the sensing means, and further connected to the display means, said contact indicating means being capable of indicating paper contact by the athlete with the sensing means.

* * * * *

UNITED STATES PATENT AND TRADEMARK OFFICE
CERTIFICATE OF CORRECTION

PATENT NO. : 4,502,489
DATED : March 5, 1985
INVENTOR(S) : William W. Alston, Jr.

It is certified that error appears in the above—identified patent and that said Letters Patent is hereby corrected as shown below:

In the ABSTRACT, line 6 "stimulates" should read --simulates--.

At column 14, line 61 "paper" should read --proper--.

Signed and Sealed this

Seventh Day of January 1986

[SEAL]

Attest:

Attesting Officer

DONALD J. QUIGG

Commissioner of Patents and Trademarks